United States Patent [19]

LeBel

[11] Patent Number: 4,871,611
[45] Date of Patent: Oct. 3, 1989

[54] BREATHABLE BACKING OR RELEASE LINER AND PROCESS FOR FORMING THE SAME

[75] Inventor: Andrew P. LeBel, Aurora, Ill.

[73] Assignee: Mead Release Products, Inc., West Chicago, Ill.

[21] Appl. No.: 63,799

[22] Filed: Jun. 23, 1987

Related U.S. Application Data

[63] Continuation of Ser. No. 799,215, Nov. 15, 1985, abandoned.

[51] Int. Cl.$^4$ .............................................. B32B 7/00
[52] U.S. Cl. .................................. 428/266; 427/394; 428/274; 428/290; 428/352
[58] Field of Search ............... 428/266, 274, 290, 352; 427/394

[56] References Cited

U.S. PATENT DOCUMENTS

| | | | |
|---|---|---|---|
| 3,121,021 | 2/1964 | Copeland | 117/122 |
| 3,364,063 | 1/1968 | Satas | 117/98 |
| 3,523,846 | 8/1970 | Muller | 156/78 |
| 3,677,788 | 7/1970 | Zirnite | 117/11 |
| 4,202,925 | 5/1980 | Dabroski | 128/156 |
| 4,427,737 | 1/1984 | Cilento et al. | 428/315.7 |
| 4,537,811 | 8/1985 | Nablo | 428/166 |

OTHER PUBLICATIONS

Hurst, "Production of Electron Beam Cured Silicone Release Paper and Film", Radcure 83.
Cyterski, "Radiation-Curable Release Coating", Radcure '84.
Eckberg, "Radiation Curable Silicones", Radcure '84.

*Primary Examiner*—Marion C. McCamish
*Attorney, Agent, or Firm*—Smith & Schnacke

[57] ABSTRACT

A breathable backing or release liner comprising a breathable, woven or non-woven support member having a silicone-release coating on essentially only one side thereof, said coating being formed by applying a radiation-curable composition containing a polysiloxane to one side of said support and exposing said composition to radiation such that said composition does not substantially penetrate said support.

20 Claims, 1 Drawing Sheet

BREATHABLE BACKING OR RELEASE LINER AND PROCESS FOR FORMING THE SAME

This is a continuation of co-pending application Ser. No. 799,215, filed Nov. 5, 1985, now abandoned.

BACKGROUND OF THE INVENTION

The present invention relates to a breathable backing or release liner and to a process for preparing the same wherein a radiation-cured silicone release coating is provided on essentially only one surface of a woven or non-woven support and high adhesion is obtained on the opposite surface.

Breathable backings are used in a number of applications including in making breathable surgical tape and in diaper tapes for disposable diapers.

Breathable surgical tapes are the subject of several prior patents including U.S. Pat. Nos. 3,121,021 to Copeland (1964), 3,364,063 to Satas (1964), 3,523,846 to Muller (1970), 3,677,788 to Zirnite (1972), 4,202,925 to Dabroski (1980), and 4,427,737 to Cilento et al.

The patents to Zirnite and Dabroski disclose a self-wound surgical tape which is constructed with an active adhesive coating on one surface of a non-woven fabric backing or support and with a release layer on the opposite surface. According to the Zirnite disclosure, the preferred release coating is a stearyl methacrylate acrylonitrile copolymer. Silicone-release backsizes are also disclosed but considered less satisfactory. Dabroski discloses that silicone backsizes may be used, but discloses a preference for water-based backsizes for their non-penetrable viscosity. In accordance with Dabroski's preferred embodiment, two release backsizes are sequentially applied to the support. The first is a styrene ethylacrylate-butadiene copolymer. The second is a silicone-release agent which is applied after drying the first.

According to both the Zirnite and Dabroski patents, the release coatings are applied using conventional application techniques. Gravure roll coating and spray coating techniques are disclosed. The gravure roll coating technique is disclosed as the preferred means.

The silicone release coatings used in the aforementioned breathable tape backings are formed using thermally-cured solvent-based or aqueous-based coating compositions. These backings frequently do not exhibit adequate adhesion for the adhesive composition, particularly when the release coating is applied to the backing before the adhesive composition. Breathable backings, are highly permeable and readily penetrated by solvent-based or aqueous-based release coating compositions. Consequently, a portion of the release coating strikes through the backing to the uncoated opposite surface and reduces the adhesion at that surface for the adhesive composition. There is also a tendency for thermally-cured compositions to offset to the opposite surface of the backing.

While adhesion may be improved if the release coating is applied after the adhesive, the preferred method for making breathable adhesive tapes is to apply the release coating first. It is not desirable to apply the adhesive first because the adhesive-coated backing is difficult to handle and, therefore, is difficult to coat with the release coating. By contrast, the release-coated backing is easily handled and readily coated with the adhesive. In addition, in the manufacture of surgical tapes, it is particularly important to keep the adhesive clean during processing so that a sterile and aseptic product is obtained. This is very difficult to do if the release coating is applied after the adhesive.

SUMMARY OF THE INVENTION

A particular object of the present invention is to provide a breathable backing useful in surgical tapes, diaper tapes, and similar applications in which a breathable backing having release properties is desired or in providing a breathable release liner in which a silicone-release coating is present on essentially one surface of the backing and high adhesion is obtained on the opposite surface.

A related object of the present invention is to provide a method for preparing a breathable tape backing wherein penetration of the backing by a silicone-release coating and offset are minimized so as to maximize adhesion on the opposite surface.

In accordance with the present invention, a breathable backing or release liner having a release coating on essentially only one surface thereof is provided by applying a radiation-curable composition containing a polysiloxane to one surface of a breathable woven or non-woven support and curing the composition by exposure to radiation in such a manner that penetration of the backing by the polysiloxane is minimized. The preferred radiation-curable compositions contain polysiloxanes having olefinic groups and, more particularly, ethylenically unsaturated polysiloxanes. The preferred radiation is ionizing radiation such as electron beam radiation, but other forms of radiation such as actinic radiation and, particularly, ultraviolet radiation can be used.

One embodiment of the present invention resides in a breathable backing or release liner comprising a breathable, woven or non-woven support having a silicone-release coating on essentially only one side thereof, said coating being formed by applying a radiation-curable composition containing a polysiloxane to one side of said support and exposing said composition to radiation such that said composition does not substantially penetrate said support.

Another embodiment of the present invention resides in a method for manufacturing a breathable backing or release liner which comprises the sequentially performed steps of: (a) providing a breathable, woven or non-woven support, (b) applying a radiation-curable composition to one surface of said support, and (c) exposing said composition to radiation such that said composition is cured and does not substantially penetrate said support.

DETAILED DESCRIPTION OF THE INVENTION

Figure 1:
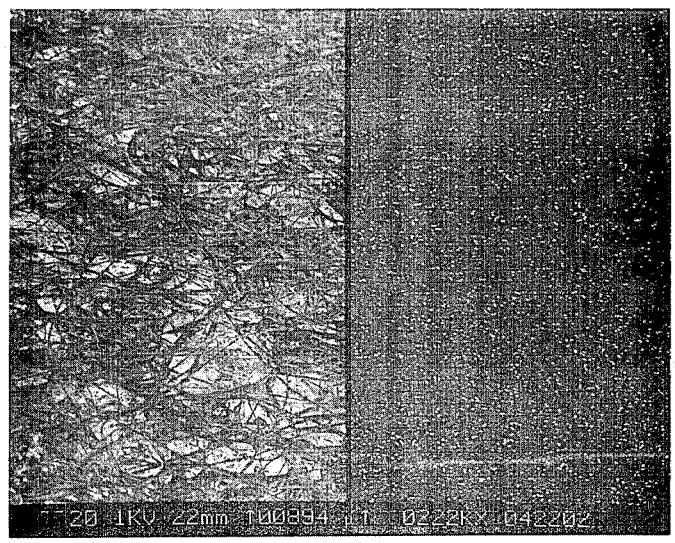
FIGS. 1 and 2 are split-screen electron microscope photographs and Si X-ray dot maps for the release-coated and uncoated surfaces of a backing in accordance with the present invention.

The support member of the breathable backing or release liner of the present invention can be a woven or non-woven breathable material and is particularly useful as a backing for a surgical tape, but as previously noted, may be used in other applications where release characteristics are desired on one side only of a breathable support member. Recent approaches to the production of wound have centered on air and moisture permeability. See U.S. Pat. No. 3,645,835 to Hodgson. Oxygen is made available to the newly-grown tissue on the wound to foster aerobic metabolism. At the same time, the wound can breathe and sweat normally.

The term "breathable support member" is used herein to define materials which are well-known in the art and characterized by their high moisture vapor transmission rate (MVTR) and/or their high air permeability. These materials are herein defined as having an MVTR greater than 250, and, more particularly, greater than 500 grams/sq.m./24 hrs./20° C./80% RH and/or an air permeability greater than 80, and, more particularly, greater than 150 ft.$^3$/min./ft.$^2$.

MVTR as used herein, is measured by the Payne Cup Method. Permeability is measured on a Gurley Permeometer as described in ASTM D-737.

A number of commercially available materials formed from a variety of fiber materials can be used as the support member. Backings formed from cellulose fibers, natural long fibers, viscose fibers, synthetic fibers (e.g., polypropylene, polyethylene, nylon, acrylic, polyester, etc.), and blends thereof, can be used. The fibers may be air laid, dry laid, wet laid, or spun laid. The fibers in the backing may or may not be bound with a binder. One material that is frequently used is a nonwoven web of interlocking cellulose and polyester fibers commercially available from C. H. Dexter as grade No. N-7601. Other useful materials include a spun bonded nylon available from Monsanto Co., under the name Cerex. A woven material such as cheese cloth can also be one-side coated with silicone resin as taught herein.

Radiation-curable compositions containing polysiloxanes are known in the art. These compositions typically contain radiation-curable polyorganosiloxanes which are capable of undergoing free radical addition polymerization. They may also contain reactive non-silicone materials in admixture with a radiation-curable material such as an ethylenically unsaturated monomers or prepolymers. These materials will affect the release characteristics. See Eckberg, R. P., *Radiation Curable Silicones,* Radcure '84 Conference Proceeding, AFP of SME, Sept. 10-13, 1984, and Cyterski, C., *Radiation-Curable Release Coatings,* Radcure '84 supra. Ultraviolet-curable compositions will also include a photoinitiator.

Representative examples of useful radiation-curable compositions are described in U.S. Pat. No. 4,052,529 to Bockerman (a composition containing a triorganosiloxane end-blocked polyorganosiloxane and methylvinylpolysiloxane), U.S. Pat. No. 4,306,050 to Koerner (a composition containing an acrylated organopolysiloxane and an initiator), U.S. Pat. No. 4,421,904 to Eckberg (an ultraviolet curable composition containing dialkylepoxy-terminated polydialkylepoxysiloxane copolymer and an iodonium salt), U.S. Pat. Nos. 4,435,259 to Chang and 4,311,821 to Weitemeyer (compositions containing vinylpolysiloxanes and polymethylhydrogen siloxanes and a photoinitiator), and U.S. Pat. No. 4,133,939 to Bokerman (compositions containing mercaptoalkyl containing triorganosiloxane end-blocked polydiorganosiloxane and benzophenone). U.S. Pat. Nos. 3,577,602 and 3,650,813, to Nordstrom et al., and 4,306,050 to Koerner et al. (T. H. Goldschmidt) teach methacrylated organopolysiloxanes which are curable by electron beam radiation which are also useful.

The radiation-curable compositions which are preferred for use in the present invention are essentially 100% reactive solids, solvent free, non-aqueous compositions which are sufficiently viscous that they do not readily penetrate the support and they cure quickly.

A particularly desirable radiation-curable composition is one which contains a polyorganosiloxane having terminal and/or pendent olefinic groups, and more particularly, terminal and/or pendent ethylenically unsaturated groups such as vinyl or allyl groups. One example of these polyorganosiloxanes is acrylated and methacrylated polyorganosiloxanes as described in aforementioned U.S. Pat. No. 4,306,050. These compounds are more specifically acrylated or methacrylated polydialkylsiloxanes wherein the alkyl groups are most typically methyl but may be ethyl, propyl or butyl. These polyorganosiloxanes are commercially available from T. H. Goldschmidt AG under the commercial designation TEGO Silicone Acrylates and include acrylates RC-149, RC-300, RC-450, and RC-802.

UV-curable compositions containing unsaturated organopolysiloxanes also include a photoinitiator. Any suitable photoinitiator may be used such as the well-known halogenated hydrocarbons (e.g., hexachlorobutadiene), aromatic ketones (e.g., benzophenone, benzoin ethyl ether, etc.), or azo compounds (e.g., azobisisobutyronitrile). The photoinitiators are used in conventional amounts, typically as low as 500 ppm.

The viscosity of the radiation-curable composition should be sufficiently high that it can be applied to the support and cured with minimal penetration of the support by the composition. Typical compositions have viscosities greater than 100 cps at 25° C., but lower viscosities can be used if the dwell time and coating amount are adjusted to limit their penetration. The upper limit on the viscosity is less critical. It should be sufficiently low so that the composition can be readily applied to the backing. Typically, the radiation-curable compositions have a viscosity less than 1800 cps at 25° C. The viscosity of the compositions most frequently used ranges from about 250 to 1800 cps.

The radiation-curable coating is applied to the support in an amount that provides adequate release characteristics and does not substantially reduce the MVTR or permeability of the support or penetrate to the opposite surface of the backing. While any application of a coating will reduce MVTR and permeability somewhat, the coating should be applied at a rate which does not reduce MVTR or permeability more than about 10%. Depending on the coating, the radiation-curable coating is usually applied in an amount of about 0.5 to 1.0 pounds/3000 sq. ft.

The coating can be applied to the support by any suitable method such as brushing, spraying, air knife, kiss roll, gravure roll, etc. Methods such as dip coating which coat both sides of the support or methods which tend to cause the coating to penetrate the support cannot be used.

The release coating is cured by exposure to ionizing or actinic radiation. The preferred radiation is electron beam radiation, but other forms of radiation, particularly ultraviolet radiation, can be used. The radiation conditions are adjusted in a manner well-known in the art to provide an essentially complete, and nearly instantaneous, cure of the release coating. Radiation is conventionally performed in an oxygen-free environment. Electron beam systems used in the present invention typically employ exposure times of about 10 to 50 milliseconds, electron energies of about 150 to 200 keV and dose rates of about 1 to 5 Megarads.

In forming the backing of the present invention, it is particularly important to control the time between application of the release coating composition and its exposure to radiation (hereinafter "dwell time"). Dwell time can be controlled by controlling the speed of the web and the distance between the coater and the radiation source. At the same time, the radiation conditions are adjusted based on the speed of the web and the coating amount to ensure that the release coating is cured completely. It has been found that dwell time should not be greater than 5 seconds. Typically, it ranges from about 1 to 4 seconds.

The release-coated backing of the present invention is characterized by minimum penetration of the web, essentially one-side-only coating, and high adhesion at the uncoated surface. These properties are reflected in its MVTR and permeation value. The coated backing of the present invention has MVTR and air permeability which are approximately equal to those of the uncoated backing. As indicated above, coating conditions and amounts are adjusted such that the values for the release-coated backing are not more than 10% less than those of the uncoated backing. In use, the application of the adhesive to the backing will reduce permeability substantially more than the application of the release coating in the present invention.

The breathable backing of the present invention is useful in forming surgical tapes, diaper tapes, and in similar applications in which a breathable support having one-sided release characteristics is desired including applications in which is functions as a release liner. The backings are typically coated on their non-release surface with a pressure-sensitive adhesive in a conventional manner. For this purpose, conventional pressure-sensitive adhesives may be used.

The one-sided nature of the release coating (or hold out) can be observed in the difference in pull force between the coated and uncoated surfaces and in an X-ray dot count for silicone on the uncoated side of the support.

Figure 2:
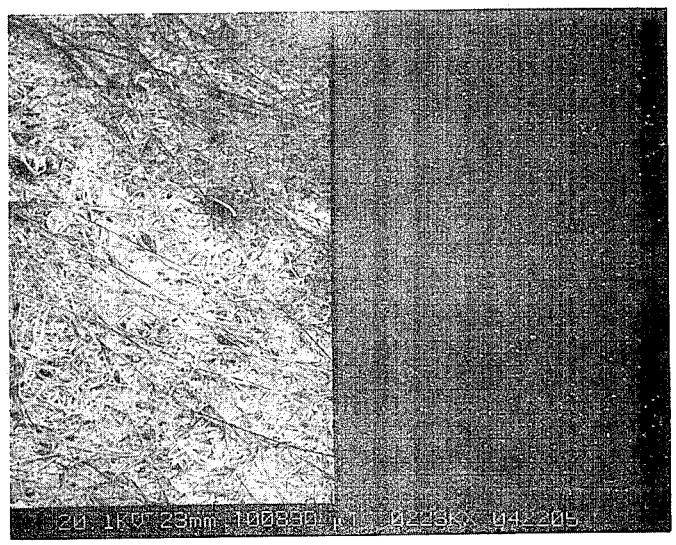

Scanning electron microscopy was used to observe surface coverage of the coated and uncoated surfaces of a backing prepared in accordance with the present invention on a Cerex 0.85 oz. non-woven support member. FIG. 1 is a split-screen electron microscope photograph of the mapped area (left) and the silicone distribution (right) for the release-coated side of the support. FIG. 2 is an electron microscope photograph of the mapped area (left) and the silicone distribution (right) for the uncoated side of the support. The electron microscope photographs illustrate the one-sided nature of the release coating which is achieved in accordance with the present invention. X-ray counts of the silicone on the coated and uncoated surfaces of the support were made using an X-ray microprobe. The silicone count on the coated surface was 4211. The silicone count on the uncoated surface was 1220. A silicone count was also made of the uncoated raw stock and determined to be 1062. This shows that essentially none of the applied silicone-release coating penetrates to the uncoated side of the support in accordance with the present invention.

EXAMPLE 1

A non-woven fabric (Cerex 0.85 oz. available from Monsanto Co.) was coated with T. H. Goldschmidt RC-450 silicone acrylate in a coating amount of 0.75 lbs./3000 sq. ft. The coating was cured by exposure to an electron beam in an inert atmosphere containing less than 500 ppm oxygen in a dosage of 1.0 megarads. The dwell time between application of the coating and exposure to the electron beam was 1.45 seconds. Adhesion to the release-coated and uncoated surfaces was measured using the following technique.

An adhesive tape was prepared by casting National Starch 80-1068A acrylic pressure-sensitive adhesive on a 0.001 inch polyester film in a wet thickness of about 0.0033 inch. The adhesive coating was allowed to dry at ambient temperature for 5 minutes and cured in an air circulating oven for 10 minutes at 158° F. After curing, the tape was allowed to cool at least 15 minutes.

The pressure-sensitive tape prepared as above was laminated to the release-coated and uncoated surface of the backing using a roller which applies a pressure of 4.5 lbs. to the back of the backside of the adhesive tape so as to exclude any air bubbles between the adhesive tape and the test backing. The pressure-sensitive tape was allowed to remain on the backing 15 minutes whereupon the laminate was mounted on a TLMI flat bed tester manufactured by Test Machine Inc. The tape was removed from the backing at a pull speed of 12 in./min. and at a pull angle of 135°. Pull force was reported in units grams/2-inch width. The peel force on the release-coated surface of the backing was 2–6 g/2 inch width. On the other hand, at the uncoated surface, the peel force was 250–300 g/2 inch width at which point the substrate split, i.e., the adhesive did not delaminate from the substrate.

Having described the invention in detail and by reference to preferred embodiments thereof, it will be apparent that modifications and variations are possible without departing from the scope of the invention defined in the appended claims.

What is claimed is:

1. A breathable backing or release liner comprising a breathable, woven or non-woven support member having a silicone-release coating on essentially only one side thereof, said coating being formed by applying a radiation-curable composition containing a polysiloxane to one side of said support and exposing said composition to radiation such that said composition does not substantially penetrate said support, and said support member having a moisture vapor transmission rate greater than 250 g/sq.m./24 hrs./20° C./80% RH and air permeability greater than 80 cu. ft./min./sq. ft.

2. The backing or liner of claim 1 wherein said support has a moisture vapor transmission rate greater than 250 g/sq. m/24 hrs./20° C./80% RH.

3. The backing or liner of claim 2 wherein said support has an air permeability greater than 80 ft.$^3$/min./ft.$^2$.

4. The backing or liner of claim 3 wherein said radiation is electron beam radiation.

5. The backing or liner of claim 4 wherein said polysiloxane includes ethylenically unsaturated groups.

6. The backing or liner of claim 5 wherein said coating is applied to said support in an amount of about 0.5 to 1.0 pound per 3000 sq. ft.

7. The backing or liner of claim 6 wherein said coating composition is essentially solvent free and non-aqueous.

8. The backing or liner of claim 7 wherein the dwell time of said composition on said support is less than about 5 seconds.

9. The backing or liner of claim 8 wherein said support is a non-woven fabric.

10. The backing or liner of claim 8 wherein said support is a woven fabric.

11. A process for preparing a breathable backing or release liner which comprises the sequentially performed steps of:
 (a) providing a woven or non-woven breathable support member having two sides, said support member having a moisture vapor transmission rate greater than 250 g/sq.m./24 hrs./20° C./80% RH and /or an air permeability greater than 80 cu. ft./min./sq. ft.,
 (b) applying a radiation curable composition containing a polysiloxane to one side of said support member, and
 (c) exposing said radiation curable composition to radiation to cure said composition, said steps (b) and (c) being conducted in such a manner that said composition does not substantially penetrate said support member.

12. The process of claim 11 wherein said support has a moisture vapor transmission rate greater than 250 g/sq. m/24 hrs./20° C./80% RH.

13. The process of claim 12 wherein said support has an air permeability greater than 80 ft.$^3$/min./ft $^2$.

14. The process of claim 13 wherein said radiation is electron beam radiation.

15. The process of claim 14 wherein said coating is applied to said support in an amount of about 0.5 to 1.0 pound per 3000 sq. ft.

16. The process of claim 15 wherein said said coating composition is essentially solvent free and non-aqueous.

17. The process of claim 16 wherein the dwell time of said composition on said support is less than about 5 seconds.

18. The process of claim 17 wherein said polysiloxane includes ethylenically unsaturated groups.

19. The process of claim 18 wherein said support is a non-woven fabric.

20. The process of claim 18 wherein said support is a woven fabric.

* * * * *